(12) United States Patent  
Salvi et al.

(10) Patent No.: US 7,235,582 B2
(45) Date of Patent: Jun. 26, 2007

(54) BASIC SALT OF THIOCTIC ACID WITH L-CARNITINE

(75) Inventors: Annibale Salvi, Milan (IT); Flavio Villani, Parma (IT); Antonio Nardi, Dungnano (IT); Bruno De Angelis, Treviglio (IT)

(73) Assignee: Laboratorio Chimico Internazionale S.p.A., Milan (IT)

( * ) Notice: Subject to any disclaimer, the term of this patent is extended or adjusted under 35 U.S.C. 154(b) by 412 days.

(21) Appl. No.: 10/698,451

(22) Filed: Nov. 3, 2003

(65) Prior Publication Data

US 2004/0214879 A1    Oct. 28, 2004

(51) Int. Cl.
*A61K 31/385* (2006.01)
*A61K 31/195* (2006.01)
*C07D 339/04* (2006.01)

(52) U.S. Cl. .................. 514/440; 514/561; 549/39
(58) Field of Classification Search ............ 514/440, 514/561; 549/39
See application file for complete search history.

(56) References Cited

U.S. PATENT DOCUMENTS 5,916,912 A    6/1999    Ames et al.

FOREIGN PATENT DOCUMENTS

| FR | 4512 | 11/1966 |
|----|------|---------|
| WO | WO 99/55331 | 11/1999 |
| WO | WO 02/17735 | 3/2002 |
| WO | WO 02/30917 | 4/2002 |
| WO | WO 02/30918 | 4/2002 |
| WO | WO 02/30919 | 4/2002 |

OTHER PUBLICATIONS

PCT Search Report for PCT Application No. PCT/EP 03/12179, Feb. 13, 2004.

*Primary Examiner*—James O. Wilson
*Assistant Examiner*—Ebenezer Sackey
(74) *Attorney, Agent, or Firm*—Pearl Cohen Zedek Latzer LLP

(57) ABSTRACT

Salt of thioctic acid with L-carnitine with the formula:

$$AY(X)_x$$

where A is

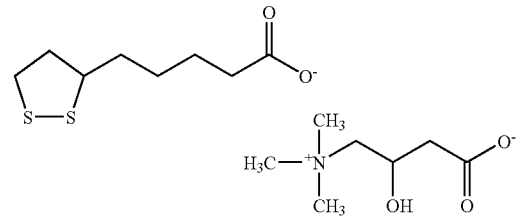

where Y is the cation of an alkaline metal, of an alkaline earth metal or is a quaternary ammonium group,
X is A or $OH^-$,
x is equal to 0 when Y is the cation of an alkaline metal or a quaternary ammonium group and equal to 1 when Y is an alkaline earth metal.

14 Claims, No Drawings

BASIC SALT OF THIOCTIC ACID WITH L-CARNITINE

PRIOR APPLICATION DATA

This application claims foreign priority from Italian Application No. MI2003A00831, filed on Apr. 22, 2003.

FIELD OF THE INVENTION

The present invention relates to a new salt of thioctic acid with L-carnitine and to a process for its preparation.

STATE OF THE ART

L-carnitine is a mitochondrial metabolite that performs a fundamental role in the oxidative metabolism of fatty acids.

Thanks to its capacity to increase the energy production of cells, this molecule may be used in numerous applications both as active pharmaceutical ingredient and as dietary supplement. L-carnitine is used, for example, as adjuvant in treating cardiomyopathies and ischaemic cardiovascular diseases, as a tonic and, in athletes, to improve muscle functionality.

The use of L-carnitine in association with an anti-oxidant and in particular with thioctic acid is particularly advantageous as it allows an increase in cellular metabolism to be obtained without incurring a concomitant increase in the production of reactive oxygen species.

Nonetheless, administering these two active ingredients in separate units of dosage is not easy for the patient, also in view of the fact that various administrations of both are required throughout the day.

In order to solve this problem the French medicament patent number 4512 M proposed the administration of an acid salt between L-carnitine and thioctic acid. Nonetheless, no example of the process for preparation of said salt is given in the patent. In fact, as the applicant proves in the examples from 4 to 6 hereunder, the acid form described in this document cannot be prepared.

A further solution to the aforesaid problem was proposed in the U.S. Pat. No. 5,916,912 wherein the L-carnitine and the thioctic acid are contained in the same unit of dosage. Nonetheless, in the only example of embodiment in this patent both active ingredients are in acid form, which leads to problems both of bio-availability and tolerability. Moreover, the production of a pharmaceutical form of this type also causes problems from the technical-pharmaceutical point of view. In fact, as it is difficult to attain perfect mixing of L-carnitine with Thioctic Acid, there is a variability in the weight ratio and titre of the two active ingredients in pharmaceutical units of the same batch.

SUMMARY OF THE INVENTION

The applicant has now found a salt of L-carnitine with thioctic acid that allows combined administration of the two active ingredients without incurring the problems mentioned hereinbefore.

The present invention therefore relates to a basic salt of L-carnitine with thioctic acid and to pharmaceutical compositions and dietary supplements containing it. The present invention also relates to a process for the preparation of the aforesaid salt.

DETAILED DESCRIPTION OF THE INVENTION

The object of the present invention is a salt with the formula:

where A is

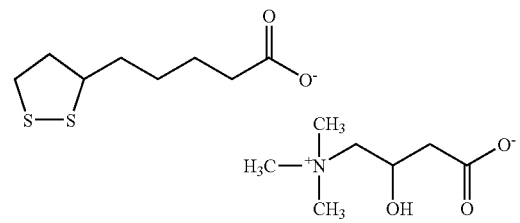

where Y is the cation of an alkaline metal, of an alkaline earth metal or is a quaternary ammonium group, X is A or OH$^-$, x is equal to 0 when Y is the cation of an alkaline metal or a quaternary ammonium group and equal to 1 when Y is an alkaline earth metal.

The quaternary ammonium cation is a tetraalkyl ammonium cation wherein the alkyl groups equal or different from each other are linear or branched and have from 1 to 10 carbon atoms.

The salt of the invention comprises thioctic acid in raceme form or in an optically active form, such as R(+)-thioctic, or S(−)thioctic acid. Thioctic acid in raceme form or optically active in R(+) or S(−) form is available on the market or can be prepared according to the techniques described in WO0230917, WO0230918 and WO0230919 respectively, in the name of the same applicant.

When L-carnitine and thioctic acid are administered as a basic salt according to the present invention they have a high level of bio-availability.

The present invention also relates to a pharmaceutical composition and to a dietary supplement comprising as active substance a salt according to the invention together with suitable excipients and/or diluents.

A further object of the present invention is a process for the preparation of the aforesaid salt comprising the following stages:

i) a solution is prepared of an alkaline, alkaline earth or quaternary ammonium salt of L-carnitine in a linear or branched $C_1$–$C_5$ alcohol, preferably methanol, said solution having a L-carnitine concentration between 10% and 30% w/v;

ii) the solution of stage a) is slowly added to a solution of thioctic acid, with a concentration between 5% and 15%, in a solvent chosen from ketones with b.p. above 75° C., esters with b.p. above 75° C., acetonitrile and linear or branched alcohols with a number of carbon atoms above 3, and iii) the salt of formula (I) is isolated.

The range of concentrations indicated in stage (a) of the process of the present invention is critical. In fact, by using concentrations higher than 30% the L-carnitine added drop-wise to the batch containing thioctic acid precipitates directly without forming the salt, while by using solutions more than 10% diluted there is a considerable loss of productivity.

Preferably, in the mixture obtained in stage b) the molar ratio between the thioctic acid and the L-carnitine is between 0.85 and 1.15.

According to a particularly preferred application, stage c) comprises the following operating phases:

א) the solvent in which the L-carnitine was dissolved is removed partially by vacuum distillation;

ב) the same solvent in which the thioctic acid was dissolved is added, preferably in a quantity necessary to substitute the solvent removed in stage i);

ג) the mixture is cooled to a temperature between 0 and 30° C. and left under stirring until complete precipitation; and ד) the precipitate obtained is separated.

Preferably, after stage iv) the precipitate is washed, to eliminate any impurities, and dried.

The invention shall now be better illustrated from the experimental examples hereunder, which however do not limit the scope of the invention.

EXAMPLES

Example 1

50.5 g (0.245 mol) of thioctic acid are dissolved in 750 ml of methyl ethyl ketone at 20–25° C. A solution of 15.5 g of potassium hydroxide pellets (0.249 mol) and 39.5 g (0.245 mol) of L-carnitine in 200 ml of methyl alcohol are added dropwise in 15–20 minutes.

After this, the solution is heated to 30°–35° C. and the solvent is distilled at low pressure to reach an internal volume of 330–350 ml (equal to about ⅓ of the initial volume).

The product starts to precipitate when about one half of the volume is removed by distillation.

After complete distillation 600 ml of methyl ethyl ketone are added and the mixture is left under stirring at 25°–30° C. for 30 minutes.

The mixture is cooled to 0.5° C. and kept at this temperature for 1 hour.

The solid is filtered, washed with 200 ml of methyl ethyl ketone and dried under vacuum at 50° C. for 24 hours.

77 g of thioctic-carnitine-potassium salt with a purity, measured by HPLC, of 98% is obtained.

The product obtained was characterized by $H^1$-NMR and MASS analysis.

$H^1$-NMR Analysis

δNMR: 4.51 ppm, 1H, m (—C$\underline{H}$—(OH)—, carnitine); 3.68 ppm, 1H, m (—C$\underline{H}$—(S)—, thioctic); 3.38 ppm, 2H, m (—N—(CH$_3$)$_3$—C$\underline{H}_2$, carnitine) 3.18 ppm, 2H, m (methylene in position 2 of the thioctic acid ring) 3.18 ppm, 9H, s (—N—(C$\underline{H}_3$)$_3$—CH$_2$—, carnitine); 2.45 ppm, 1H, m (one of the 2 atoms of hydrogen in position 3 of the thioctic acid ring); 2.39 ppm, 2H, dd (—C$\underline{H}_2$—COO$^-$, carnitine); 2.14, 2H; t (C$\underline{H}_2$—(COOH) thioctic acid); 1.96 ppm, 1H, m (one of the two atoms of hydrogen in position 3 of the thioctic acid ring), 1.3–1.8 ppm, 6H, m (—CH$_2$—CH$_2$—C$\underline{H}_2$—,thioctic acid).

Mass

The following peaks are observed:

206 (m/e): molecular peak of the thioctic 161 (m/e): molecular peak of the Carnitine Example 2

10.1 g (0.049 ml) of thioctic acid are dissolved in 150 ml of methyl ethyl ketone at 20–25° C. A solution of 8.9 g of 30% sodium methylate (0.049 ml) and 7.9 g (0.049 ml) of L-carnitine in 40 ml of methyl alcohol are added dropwise in 15–20 minutes.

After this, the solution is heated to 30–35° C. and the solvent is distilled under low pressure to reach an internal volume of about 100 ml (equal to half the initial volume). During distillation the product precipitates.

After complete distillation 100 ml of methyl ethyl ketone are added and left under stirring at 25–30° C. for 30 minutes.

The solid is filtered, washed with 60 ml of methyl ethyl ketone and dried under vacuum at 50° C. for 24 hours.

16 g of thioctic-carnitine-sodium salt with a purity, measured by HPLC analysis, of 97.6% is obtained.

Example 3

100 g of thioctic acid are dissolved in 1300 ml of methyl ethyl ketone at a temperature of 17° C. 78 g of L-carnitine and 29.5 g of potassium hydroxide dissolved in 300 ml of methanol are added dropwise in 5 minutes. After maintaining the solution under stirring for 5 minutes one half of the volume solvent is removed by distillation under vacuum without exceeding 35° C. in the boiler. After complete distillation 400 ml of methyl ethyl ketone are added dropwise in 30 minutes at 20° C. The resulting suspension is cooled to 15° C. and kept at this temperature for 2 hours. The precipitate formed is filtered under an inert atmosphere washing the solid with 200 ml of methyl ethyl ketone. 370 g of a yellowish solid is obtained, which is dried in an oven under vacuum at 40° C. for 20 hours, to obtain 122 g of dry product.

The product obtained has an HPLC titre in thioctic acid equal to 51.6% (theoretical 50.8%). Moreover, the pH of an aqueous solution at 10% of the product obtained is equal to 8.14.

Example 4

28 g of thioctic acid, 22 g of L-carnitine and 150 ml of methanol are stirred at a temperature of 20–25° C. until complete dissolution. The solvent is removed by distillation under vacuum at a temperature below 40° C. until and a thick or oily yellow residue (52 g) is obtained. The residue is recovered with 200 ml of water without managing to obtain a complete solution; a big gummy agglomerate (polymer of the thioctic acid) separates in the solution.

Example 5

28 g of thioctic acid, 22 g of L-carnitine and 150 ml of methanol are stirred until complete dissolution. The solvent is removed by distillation under vacuum at a temperature below 40° C. until a thick yellow residue is obtained. The residue is recovered with 200 ml of acetone and left under stirring for one hour. The resulting suspension is filtered and 23 g of a damp product (white solid) are obtained.

TLC analysis shows that the product obtained is L-carnitine while thioctic acid is absent.

The yellow mother liquors from filtration are concentrated to obtain a residue giving 30 g of thick oil.

TLC analysis shows that the oily residue is thioctic acid.

Example 6

19.5 g of L-carnitine is dissolved in 100 ml of methanol. The solution obtained is added dropwise in 25 minutes to a solution of 25 g of thioctic acid in 190 ml of methyl ethyl ketone and stirred at a temperature of 10–15° C. After maintaining the solution under stirring for 15 minutes ⅔ of the solvent is removed by distillation undr vacuum without exceeding 35° C. in the boiler. After complete distillation, 300 ml of methyl ethyl ketone is added dropwise in 15 minutes at 20° C. The resulting suspension is cooled over 3 hours to 3° C. and then filtered in an inert atmosphere washing the solid with 100 ml of methyl ethyl ketone. 15.1 g of white solid is obtained, which is dried in an oven under vacuum at 40° C. for 20 hours, obtaining 13.8 g of dry product.

HPLC analysis shows that the product obtained is L-carnitine with traces (about 0.035%) of thioctic acid.

What is claimed is:

1. A salt of a thioctic acid with L-carnitine, represented by the formula:

AY(X)$_x$ where A is

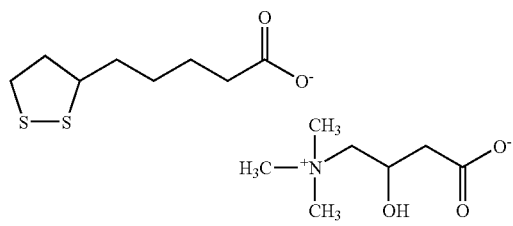

where Y is the cation of an alkaline metal, of an alkaline earth metal or is a quaternary ammonium group, X is A or OH$^{31}$, x is equal to 0 when Y is the cation of an alkaline metal or a quaternary ammonium group and equal to 1 when Y is an alkaline earth metal.

2. Salt as claimed in claim 1 wherein Y is chosen from the group consisting of Na$^+$ and K$^+$.

3. Salt as claimed in claim 1 wherein Y is chosen from the group consisting of Mg$^{++}$ and Ca$^{++}$.

4. Salt as claimed in claim 1 wherein Y is a tetralkyl ammonium wherein the alkyl groups equal or different among each other are linear or branched and have from 1 to 10 carbon atoms.

5. Salt as claimed in claim 1 wherein the thioctic acid is in racemic form.

6. Salt as claimed in claim I wherein the acid is in optically active form and chosen from —R(+) or S(–) thioctic acid.

7. Process for the preparation of a salt as claimed in claim 1 comprising the following stages:

a) preparing a solution of an alkaline, alkaline earth metal or a quaternary ammonium salt of L-carnitine in a linear or branched C$_1$–C$_5$ alcohol, said solution having a L-carnitine concentration between 10% and 30% w/v;

b) adding slowly the solution of stage a) to a solution of thioctic acid, with a concentration between 5% and 15%, in a solvent chosen from the group consisting of ketones with b.p. above 75° C., esters wit b.p. above 75° C., acetonitrile and linear or branched alcohols with a number of carbon atoms above 3; and c) isolating the salt of formula (I) from the reaction mixture.

8. Process as claimed in claim 7 wherein in stage a) said alcohol is methanol.

9. Process as claimed in claim 7 wherein in stage b) the solution of L-carnitine is added to the solution of thioctic acid in such a quantity that in the final mixture the molar ratio between the thioctic acid and the L-carnitine is comprised between 0.85 and 1.15.

10. Process for the preparation of a salt as claimed in claim 1 comprising the following stages:

a. preparing a solution of an alkaline, alkaline earth metal or a quaternary ammonium salt of L-carnitine in a linear or branched C$_1$–C$_5$ alcohol, said solution having a L-carnitine concentration between 10% and 30% w/v;

b. adding slowly the solution of stage a) slowly to a solution of thioctic acid, with a concentration between 5% and 15%, in a solvent chosen from the group consisting of ketones with b.p. above 75° C., esters with b.p. above 75° C., acetonitrile and linear or branched alcohols with a number of carbon atoms above 3, and c. isolating the salt of formula (I) from the reaction mixture, said stage c) comprising the following operating phases:

i) removing partially the solvent in which the L-carnitine was dissolved by distillation under vacuum;

ii) adding the same solvent in which the thioctic acid was dissolved;

iii) cooling the mixtures to a temperature between 0 and 30° C.;

iv) separating the precipitate obtained.

11. Process as claimed in claim 10 wherein in stage ii) the solvent is added in the quantity required to replace the solvent removed in stage i).

12. Process as claimed in claim 10 wherein the product obtained in stage iv) is washed and dried.

13. Pharmaceutical composition comprising the salt as claimed in claim 1 together with suitable excipients or diluents.

14. Dietary supplement comprising the salt as claimed in claim 1 together with suitable excipients or diluents.

* * * * *